United States Patent [19]
Nemser et al.

[11] Patent Number: 6,126,721
[45] Date of Patent: Oct. 3, 2000

[54] OXYGEN ENRICHED AIR SUPPLY APPARATUS

[75] Inventors: Stuart Marshall Nemser; Louis Himelreich, both of Wilmington, Del.

[73] Assignee: Compact Membrane Systems, Inc., Wilmington, Del.

[21] Appl. No.: 09/192,669

[22] Filed: Nov. 16, 1998

Related U.S. Application Data

[63] Continuation-in-part of application No. 09/143,310, Aug. 28, 1998, abandoned.

[51] Int. Cl.$^7$ .................................................. B01D 53/22
[52] U.S. Cl. ............................. 95/54; 96/4; 96/8; 96/13
[58] Field of Search ............................. 95/45, 54, 4, 6, 95/8, 12, 13

[56] References Cited

U.S. PATENT DOCUMENTS

| | | | |
|---|---|---|---|
| 3,369,343 | 2/1968 | Robb | 96/6 X |
| 3,930,813 | 1/1976 | Gessner | 95/54 |
| 3,930,814 | 1/1976 | Gessner | 95/54 X |
| 3,976,451 | 8/1976 | Blackmer et al. | 95/54 X |
| 4,174,955 | 11/1979 | Blackmer et al. | 55/158 |
| 4,230,463 | 10/1980 | Henis et al. | 55/16 |
| 4,632,677 | 12/1986 | Blackmer | 55/158 |
| 4,938,778 | 7/1990 | Ohyabu et al. | 623/66 |
| 5,051,113 | 9/1991 | Nemser | 55/16 |
| 5,051,114 | 9/1991 | Nemser et al. | 55/16 |
| 5,053,059 | 10/1991 | Nemser | 95/54 |
| 5,147,417 | 9/1992 | Nemser | 55/16 |
| 5,158,584 | 10/1992 | Tamura | 95/54 X |
| 5,238,471 | 8/1993 | Blanchet-Fincher | 96/13 |
| 5,258,202 | 11/1993 | Pellegrino et al. | 427/235 |
| 5,388,413 | 2/1995 | Major et al. | 95/54 X |
| 5,526,641 | 6/1996 | Sekar et al. | 60/274 |
| 5,611,845 | 3/1997 | Delp, II | 96/8 X |
| 5,636,619 | 6/1997 | Poola et al. | 123/585 |
| 5,649,517 | 7/1997 | Poola et al. | 123/585 |
| 5,678,526 | 10/1997 | Cullen et al. | 123/390 |
| 5,730,780 | 3/1998 | Booth, III | 96/8 X |
| 5,746,806 | 5/1998 | Aylsworth et al. | 95/54 X |
| 5,846,291 | 12/1998 | Delp, II | 95/54 X |
| 5,902,379 | 5/1999 | Phillips et al. | 95/54 X |

FOREIGN PATENT DOCUMENTS

| | | |
|---|---|---|
| 0 649 676 | 4/1994 | European Pat. Off. . |
| 2-252609 | 10/1990 | Japan ..................... 95/54 |
| 2-263704 | 10/1990 | Japan ..................... 95/54 |
| WO 90/15662 | 12/1990 | WIPO . |

OTHER PUBLICATIONS

Lund, L.W., et al., Gas permeability of hollow fiber membranes in a gas–liquid system, *Journal of Membrane Science*, 117 (1996) 207–219.

Nemser, S., Applications of Membranes in Industry Glassy Fluoropolymer Membranes, 21st Aharon Katzir–Katchalsky Conference, Rehovot, Israel, Sep. 5–8, 1993.

Pinnau et al: J. Membrane Sci., vol. 109, pp. 125–133, 1996.

(List continued on next page.)

*Primary Examiner*—Robert H. Spitzer
*Attorney, Agent, or Firm*—Jeffrey C. Lew

[57] ABSTRACT

A portable breathing air supply apparatus uses a membrane separation module to obtain oxygen enriched air from ambient air which is blown into the module by an electrically powered fan. Oxygen enriched air is withdrawn from the permeate side of the membrane by a vacuum pump and is stored in a reservoir while the user exhales. In a preferred mode, a conserver valve in a tube leading from the reservoir to the user's mouth or nose is triggered to feed the enriched air for a preselected duration after a sensor in the tube detects onset of inhalation. Power for the electrical components can be supplied by batteries. The portable apparatus is sufficiently compact and light to be transported by persons weakened by certain chronic breathing disorders, such as chronic obstructive pulmonary disease and emphysema, and thus frees the user to roam for long periods away from a primary source of oxygen.

31 Claims, 7 Drawing Sheets

OTHER PUBLICATIONS

Compact Membrane Systems, Inc. brochurem, Soc. of Automotive Engineers Annual Mtg. Detroit, Feb. 27, 1997.

S. Nemser, et al., High Gas Flux Hollow Fiber Membranes, May 27, 1997 presentation at North American Membrane Society Annual Meeting.

S. Nemser, Compact Membrane Systems, Inc., Oct. 28, 1997, presentation at Business Communication Conference, Boston.

Compact Membrane Systems, Inc., *High Gas Flux Hollow Fiber Membranes*, Business Communications Corporation Conference, Newton, MA Oct. 29, 1996.

OXYGEN ENRICHED AIR SUPPLY APPARATUS

This is a continuation-in-part of application Ser. No. 09/143,310 filed Aug. 28, 1998, now abandoned.

FIELD OF THE INVENTION

This invention relates to an apparatus for generating oxygen enriched air. More specifically, it relates to a light weight, compact, portable apparatus using selectively permeable hollow fiber membranes to produce breathable, oxygen enriched air from ambient air.

BACKGROUND AND SUMMARY OF THE INVENTION

The inhalation of oxygen enriched air is sometimes prescribed for treatment of certain chronic breathing disorders, such as chronic obstructive pulmonary disease and emphysema. The traditional methods for generating oxygen enriched air for such treatment generally utilize stationary equipment to manufacture oxygen chemically, e.g. by electrolysis or pressure swing adsorption, or to refine oxygen from air cryogenically. Stationary sources of oxygen enriched air are unsuitable for many patients because the roaming range of the user is limited to the immediate vicinity of the enriched air supply.

Oxygen produced by a stationary source can be stored in tanks and carried by the patient to be consumed away from the source. However, oxygen is usually stored under pressure to maximize storage capacity. Storage tanks capable of holding compressed gas are normally bulky and heavy. Patients who suffer from breathing difficulty are likely to be weak and generally are not able to easily handle heavy compressed oxygen tanks. Furthermore, tank capacity normally limits usage to at most about a couple of hours away from the primary source of oxygen enriched air.

Membrane separation technology would seem to show promise for portable generation of oxygen enriched air. Oxygen in ambient air contacted with an oxygen selectively permeable membrane will preferentially permeate through the membrane to form an oxygen rich permeate fraction and an oxygen depleted, nitrogen rich retentate fraction. However, conventional enriched air delivery apparatus use membrane materials which have inadequate flux to provide enough enriched breathing air in a small unit. Also, accessory equipment such as fans and valves are utilized to permit the apparatus to function properly. Despite the advent of membrane separation technology, a compact, light weight, effective air flow capacity yet fully mobile, portable oxygen enriched air generator has been unavailable.

U.S. Pat. No. 4,632,677 describes a high humidity oxygen enricher that includes an array of membrane cells each of which is selectively permeable to permit oxygen and water vapor to permeate into chambers of the cell at a greater rate than nitrogen. The membranes are formed of silicone rubber, polymethylpentene, silicone-polycarbonate copolymer and polyphenylene ethers, for example. The figures show that wheels are utilized to move the apparatus about. The apparatus also uses an external source of electric power connected by a cable and thus is not portable. These observations imply that the bulk and weight of this oxygen enricher are substantial.

Certain amorphous copolymers of perfluoro-2,2-dimethyl-1,3-dioxole ("PDD") have recently been found to be suitable for making a membrane capable of separating air to form oxygen enriched air at high flux. Such membranes are disclosed in U.S. Pat. No. 5,051,114 which is incorporated in its entirety by reference herein.

The ability to fabricate a membrane having a very thin coating of PDD copolymer on a microporous substrate of extremely high surface-to-volume ratio such as hollow fibers was recently developed. It has now been discovered that membrane modules having multiple, PDD copolymer thinly coated hollow fiber membranes can be used to make a truly portable, oxygen enriched air supply apparatus. High oxygen flux allows the module to be small enough that adequate amounts of oxygen enriched air can be generated by processing very low volumetric rates of ambient air. Consequently, auxiliary components such as fans, pumps, tubes, valves and batteries are commensurately small and provide a portable apparatus light weight and small enough to be carried by many weak or infirm patients.

Accordingly, there is now provided an oxygen enriched air supply apparatus comprising a membrane separation module comprising an oxygen gas selectively permeable membrane defining within the module a retentate chamber on one side of the membrane and a permeate chamber on the opposite side of the membrane;

an ambient air intake fan having an exhaust port in fluid communication with the retentate chamber;

a vacuum pump having a suction port and a discharge port, the suction port being in fluid communication with the permeate chamber;

gas reservoir means for storing oxygen enriched air received from the discharge port;

breathing nozzle means for delivering oxygen enriched air to an animal;

a gas transfer tube extending from the reservoir means to the breathing nozzle means; and power supply means for providing electrical power to operate the portable oxygen enriched air supply apparatus.

There is also provided a process comprising the step of using an apparatus to produce oxygen enriched air, the apparatus comprising a membrane separation module comprising an oxygen gas selectively permeable membrane defining within the module a retentate chamber on one side of the membrane and a permeate chamber on the opposite side of the membrane;

an ambient air intake fan having an exhaust port in fluid communication with the retentate chamber;

a vacuum pump having a suction port and a discharge port, the suction port being in fluid communication with the permeate chamber;

gas reservoir means for storing oxygen enriched air received from the discharge port;

breathing nozzle means for delivering oxygen enriched air to an animal;

a gas transfer tube extending from the reservoir means to the breathing nozzle means; and power supply means for providing electrical power to operate the oxygen enriched air supply apparatus.

This invention further provides an oxygen enriched air supply apparatus comprising a membrane separation module comprising an oxygen gas selectively permeable membrane defining within the module a retentate chamber on one side of the membrane and a permeate chamber on the opposite side of the membrane;

an ambient air intake fan having an exhaust port in fluid communication with the retentate chamber;

a vacuum pump having a suction port and a discharge port, the suction port being in fluid communication with the permeate chamber;

breathing nozzle means for delivering oxygen enriched air to an animal;

a gas transfer tube extending from the discharge port to the breathing nozzle means;

a conserver valve in the gas transfer tube;

sensor means in the gas transfer tube downstream of the conserver valve for detecting the start of inhalation by the animal; and control means for operating the conserver valve to be open only for a preselected duration after start of inhalation by the animal.

DETAILED DESCRIPTION

Figures 1A, 1B:
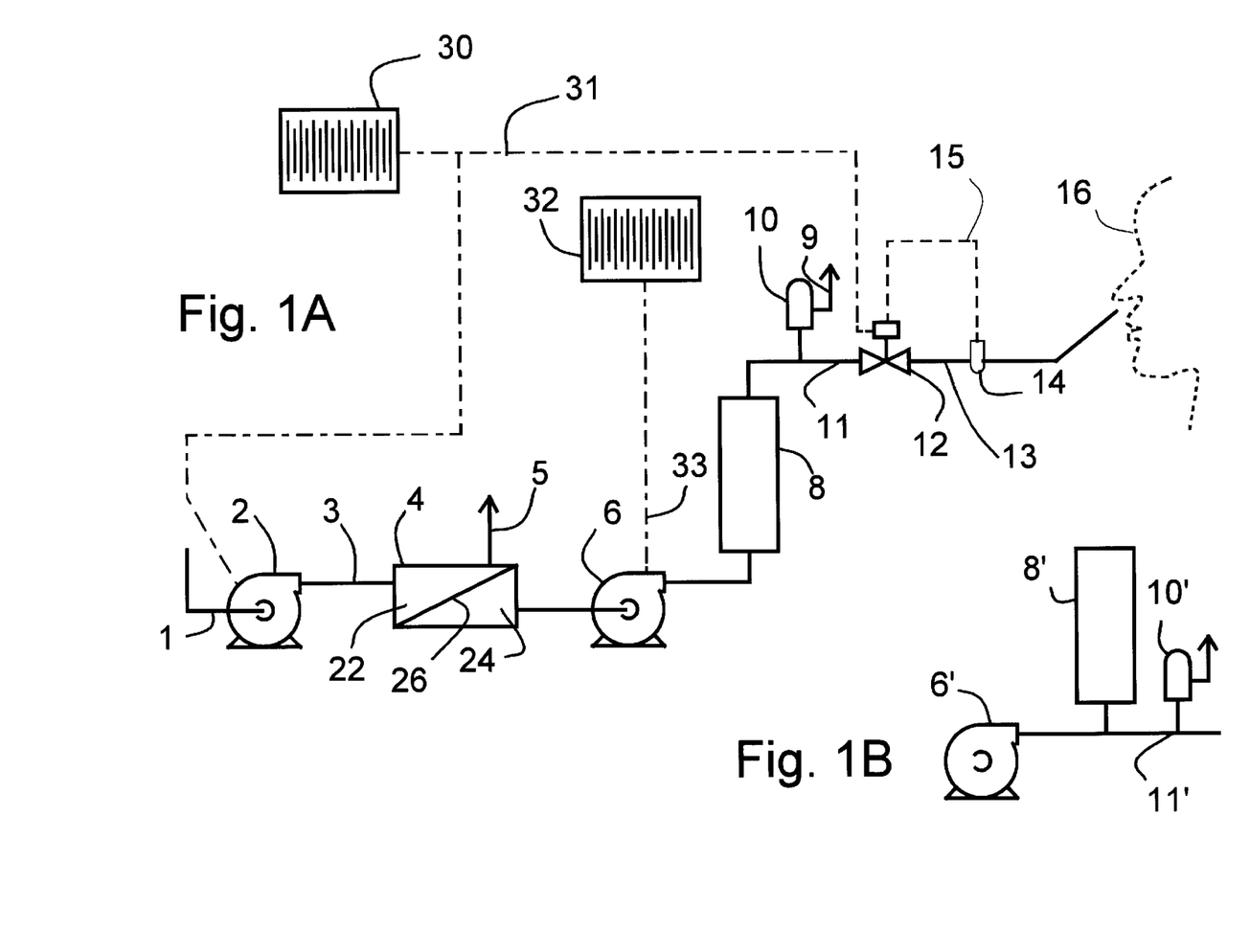
FIG. 1A is a schematic flow diagram of an embodiment of a portable oxygen enriched air supply apparatus according to this invention.
FIG. 1B is a modified form of part of the apparatus shown in FIG. 1A.

The nature of this invention can be better understood with reference to FIG. 1A which illustrates schematically an embodiment of the novel portable oxygen enriched air supply apparatus. The apparatus includes a blower 2 to continuously supply ambient air drawn into supply tube 1 to the retentate chamber 22 of a membrane module 4 via feed tube 3. The module contains a selectively gas permeable membrane 26 which separates the retentate from the permeate chamber 24. The selectively gas permeable membrane is defined by its ability to selectively permeate oxygen which produces an oxygen enriched air fraction in the permeate chamber and leaves an oxygen depleted air fraction in the retentate chamber. Incoming ambient air from supply tube 1 continuously displaces the nitrogen enriched air through vent 5. A vacuum pump 6 continuously draws on the permeate chamber 24 to increase the flux of oxygen enriched air. The vacuum pump exhausts oxygen enriched air into a reservoir 8.

The reservoir accumulates oxygen enriched air prior to discharge to the patient 16 through reservoir outlet tube 11 and breathing tube 13. The reservoir outlet tube 11 optionally includes a pressure relief valve 10 set to relieve to atmosphere through tube 9 if outlet tube pressure exceeds a preselected pressure. FIG. 1B shows a suitable alternate placement of the gas reservoir 8' in relation to the vacuum pump 6', reservoir outlet line 11' and pressure relief valve 10'. The inlet to the pressure relief valve usually is close-coupled to the reservoir and, in an embodiment, coupled in fluid communication directly to the reservoir. The purpose of the relief valve primarily is to protect the reservoir from breaking open if the flow of oxygen enriched air to the user through tubes 11 and 13 become blocked, for example, by kinking.

Reservoir outlet tube 11 connects to the inlet of conserver valve 12 which exhausts through tube 13 to a breathing nozzle (not shown) for user 16. The conserver valve is normally closed and is opened during inhalation to admit oxygen enriched air to the breathing nozzle. In a preferred embodiment, the conserver valve is opened for a preselected duration during the inhalation portion of each breathing cycle. A sensor 14 in tube 13 transmits a signal via connection 15 to the conserver valve controller at the start of inhalation. Preferably, start of inhalation is detected by the creation of a reduced pressure pulse in the breathing tube.

In one aspect, the conserver valve is set to remain open for a fixed duration commencing at the start of inhalation. The fixed duration will depend on the breathing frequency (i.e., breaths per minute) and the relative lengths of the inhalation and exhalation portions of a particular user's breathing cycle. It is common for a person to breath between about 15–20 times per minute and the typical inhale duration is about 2 seconds. For such individuals, a conserver valve open time of 1.25 seconds is preferred because it avoids losing an excessive amount of oxygen enriched air if a user increases breathing frequency to higher than average.

The use of a reservoir and conserver valve described above is advantageous for several reasons. Firstly, the reservoir dampens the flow of oxygen enriched air to the user. The user tends to perceive that the air supplied directly from the vacuum pump is blown too forcefully into the nose due to pulsations created by the pump and is therefore discomforting. Secondly, the reservoir accumulates oxygen enriched air which would otherwise be wastefully expelled during the exhalation period. By saving oxygen enriched air produced during exhalation, the accumulation function reduces the size of the membrane module needed to supply the volume of air taken in by the user. Not only does the reduced size render the module smaller and more unobtrusive, but it lowers the weight of the whole apparatus. This contributes to making the apparatus easier to carry. It is also preferable that the whole apparatus weigh less than about 15 kg.

The preferred embodiment of this invention described above includes both a gas reservoir and a conserver valve with associated sensor and conserver valve controller. In another embodiment, of these elements, only the gas reservoir is present. That is, the vacuum pump continuously supplies oxygen enriched air to the gas reservoir and a continuous flow of oxygen enriched air with pulsations damped by the reservoir passes from the reservoir to the user. In still another embodiment contemplated in accordance with this invention, of the two elements, only the conserver valve with sensor and controller is present. As the reservoir normally occupies a large volume, this reservoir-free embodiment can be particularly useful in applications in which it is desired to limit the apparatus to a small volume. In this embodiment, the vacuum pump continuously supplies oxygen enriched air to the inlet of the conserver valve which then passes the enriched air to the user for a portion of the breathing cycle. It is preferred to employ a pressure relief valve upstream of the conserver valve so that pump discharge air which builds up to high pressure when the conserver valve is closed can exhaust from the apparatus.

In another embodiment, the sensor can be used to cause the vacuum pump to operate only during a preselected portion of the inhalation period, e.g., 1.25 seconds after commencement of inhalation. In this way, pressure does not build up during the remainder of the breathing cycle. Accordingly, the conserver valve and the relief valve may be eliminated.

The apparatus includes a power supply means to operate the electrical components, i.e., the blower, the vacuum pump and the conserver valve. Preferably the power source comprises direct current batteries 30 and 32, connected to the components by circuitry 31 33, respectively. Such batteries permit the apparatus to operate in portable mode, that is, without a wired connection to a fixed source of electricity. The terms "battery" and "batteries" are used herein to encompass both single cell as well as multiple cell power storage devices. Fusing, ground wiring, and switches are not shown. The vacuum pump usually draws the most power and may need more than a single battery to drive it. Weight of the batteries is important to the utility of the apparatus. In general, the capacity of batteries is proportional to battery weight. Consequently, if the battery is too light, it may not be powerful enough to operate the apparatus for a reasonable time. However, if the batteries are too heavy, the whole unit becomes unwieldy for a weak person to carry for long distances or times. Batteries for use in this invention can be single use, disposable type cells, however, multiple use, rechargeable batteries are preferred. Many types of batteries can be used such as dry cell, nickel-cadmium, nickel-metal hydride or lithium ion batteries. Optionally, battery recharging components adapted to connect onboard rechargeable batteries to a source of alternating current electricity can be included in the apparatus. This would allow the batteries to be recharged in place rather than replaced when battery capacity has diminished through use. Although its compactness renders the novel oxygen enriched air supply apparatus highly advantageous for use in portable mode, it is contemplated that the apparatus can be used under power from a fixed source of electricity, such as a standard source of alternating current electricity or an external direct current power source. For example, it may occasionally be desired to preserve on board battery strength by tapping power from a large auxiliary battery, such as an automobile battery.

The membrane used in this invention can be any oxygen selectively permeable membrane that has an oxygen:nitrogen selectivity of at least about 1.5 while delivering an oxygen flux of at least about 600 gas permeation units ("GPU"), i.e., one GPU being equal to $1 \text{ cm}^3 \times 10^{-6}/(\text{cm}^2 \cdot \text{sec} \cdot \text{cm Hg})$. Furthermore, the membrane should be able to produce at least about 4 L per minute of air containing at least about 25 vol. % oxygen. It is also preferable that the whole apparatus weigh less than about 15 kg.

Flat sheet, pleated, spiral wound, tube and tube ribbon selectively oxygen permeable membranes are acceptable for use in this invention. It has been found that a particularly useful membrane structure employs a substrate of small diameter, microporous hollow fibers coated with a very thin layer of perfluoro-2,2-dimethyl-1,3-dioxole ("PDD")/tetrafluoroethylene ("TFE") copolymer.

In some preferred embodiments, the copolymer is copolymerized PDD and at least one monomer selected from the group consisting of tetrafluoroethylene ("TFE"), perfluoromethyl vinyl ether, vinylidene fluoride and chlorotrifluoroethylene. In other preferred embodiments, the copolymer is a dipolymer of PDD and a complementary amount of TFE, especially such a polymer containing 50–95 mole % of PDD. Examples of dipolymers are described in further detail in U.S. Pat. Nos. 4,754,009 of E. N. Squire, which issued on Jun. 28, 1988; and 4,530,569 of E. N. Squire, which issued on Jul. 23, 1985. Perfluorinated dioxole monomers are disclosed in U.S. Pat. No. 4,565,855 of B. C. Anderson, D. C. England and P. R. Resnick, which issued Jan. 21, 1986. The disclosures of all of these U.S. patents are hereby incorporated herein by reference.

The amorphous copolymer can be characterized by its glass transition temperature ("$T_g$"). The polymer property of glass transition temperature is well understood in the art. It is the temperature at which the copolymer changes from a brittle, vitreous or glassy state to a rubbery or plastic state. The glass transition temperature of the amorphous copolymer will depend on the composition of the specific copolymer of the membrane, especially the amount of TFE or other comonomer that may be present. Examples of $T_g$ are shown in FIG. 1 of the aforementioned U.S. Pat. No. 4,754,009 of E. N. Squire as ranging from about 260° C. for dipolymers with 15% tetrafluoroethylene comonomer down to less than 100° C. for the dipolymers containing at least 60 mole % tetrafluoroethylene. It can be readily appreciated that perfluoro-2,2-dimethyl-1,3-dioxole copolymers according to this invention can be tailored to provide sufficiently high $T_g$ that a membrane of such composition can withstand exposure to steam temperatures. Hence, membranes of this invention can be made steam sterilizable and thereby suitable for various uses requiring sterile materials, especially those involving oxygen enriched air for breathing. Preferably, the glass transition temperature of the amorphous copolymer should be at least 115° C.

Figure 6:
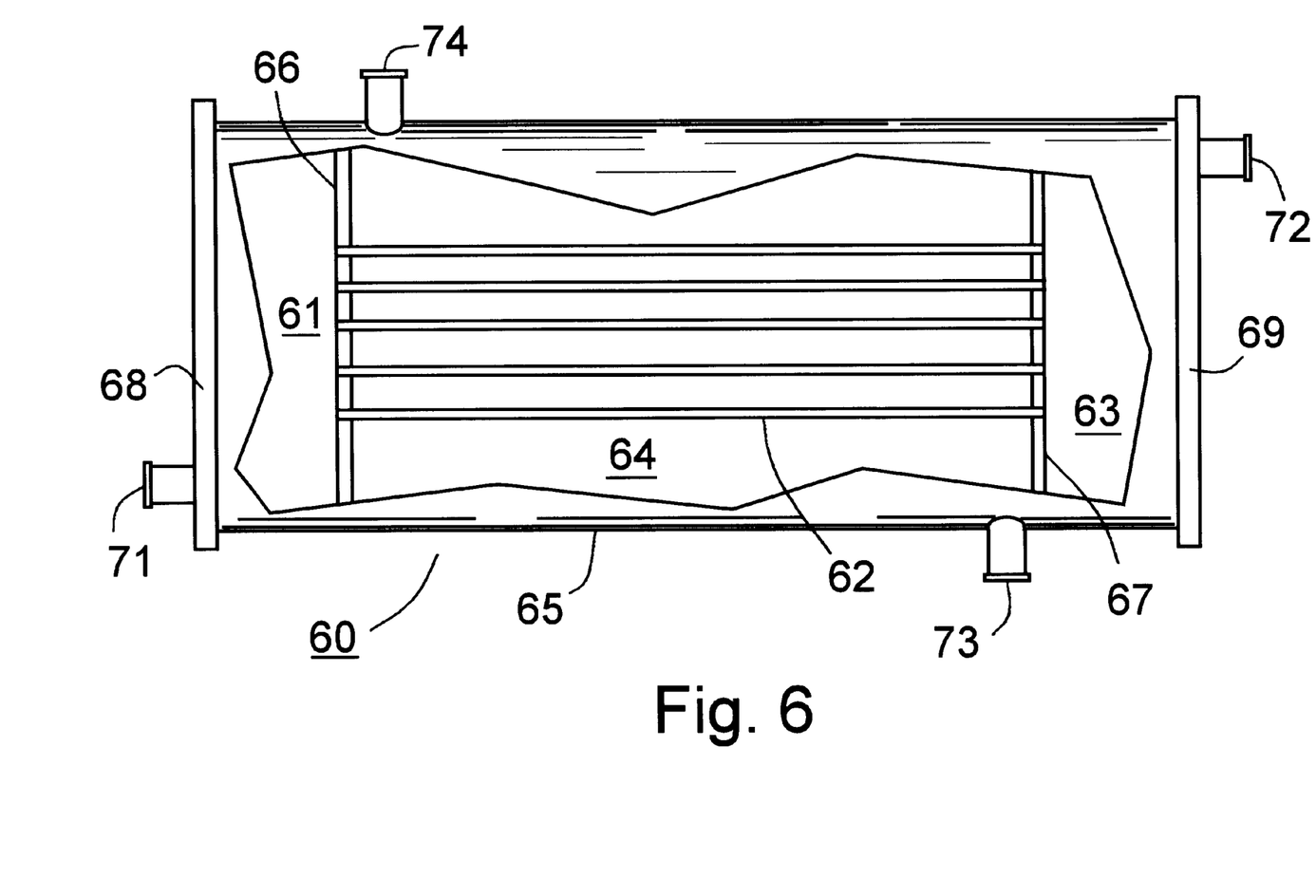
FIG. 6 is a partial section view of a preferred hollow fiber membrane module.

In a particularly preferred embodiment, the novel enriched air supply apparatus utilizes a hollow fiber membrane module illustrated in FIG. 6. This generally cylindrical membrane module 60 includes a plurality of hollow fiber membrane units 62 disposed within a shell side cavity 64 defined by the inside surface of wall 65 of the module, inlet tube sheet 66 and outlet tube sheet 67. The term "membrane module" is used herein to means an apparatus which includes a plurality of hollow fiber membrane units generally within a common housing and which units are adapted, as in a manifolded configuration, to cooperatively function with a single first fluid stream and a single second fluid stream. The spaces between end plates 68 and 69 and inlet and outlet tube sheets further define inlet and outlet plenums 61 and 63, respectively. Each hollow fiber membrane unit is a generally tubular structure including a hollow fiber substrate with a thin coating of amorphous copolymer over at least one complete surface of the fiber. That is, the fiber is coated at least on its inside or outside surface.

Ends of the membrane units terminate at the inlet and outlet tube sheets in the manner that the space within the hollow fibers is in fluid communication with the inlet and outlet plenums. The technique for mounting multiple hollow fibers in tube sheets, often called "potting" is well known in the art. This technique basically involves embedding a bundle of hollow fibers in a mass of curable polymer which is allowed to set which fixes the fiber bundle. Then the bundle of cured polymer mass and fibers is sliced to create the end of the tube sheet.

The space inside the membrane module within the inlet and outlet plenums and inside the hollow fibers may be designated as the "tube side" of the module. The membrane unit ends are sealed to the tube sheets so that the space within the fibers is isolated from the shell side cavity 64. The membrane module is further equipped with first fluid inlet and outlet ports 71 and 72, respectively. First fluid inlet port 71 is in fluid communication with inlet plenum 61 and first fluid outlet port 72 is in fluid communication with outlet plenum 63.

The membrane module also has ports mounted on the shell of the module which open through the wall 65 in fluid communication with the shell side cavity 64. In the illustrated embodiment, second fluid inlet port 73 and second fluid outlet port 74 are shown. As illustrated, second fluid inlet and outlet ports are at opposite ends of the module. Placement of the second fluid ports can be at different locations depending upon the use of the module. For example, both second fluid ports can be at the same end of the module, that is near the inlet tube side end or the exit tube side end. Optionally, at least one first or second fluid port can be sealed closed or not installed on the module, again depending upon the method with which the membrane module is utilized.

In a preferred configuration of a membrane module shown in FIG. 6 in the enriched air supply apparatus, inlet air is made to flow through the tube side. The inlet air enters through first fluid inlet port 71, and is permitted to enter inlet plenum 61. The incoming air thus passes through the interior of hollow fibers 62 the inside surfaces of which are coated with a thin layer of selectively gas permeable membrane material. An oxygen enriched fraction of air in contact with the membrane material permeates to the shell side. Thus, the tube and shell sides of such configured membrane separation module correspond to the retentate and permeate cavities, respectively. Oxygen depleted/nitrogen enriched retentate air remaining in the hollow fibers is discharged through outlet plenum 63 via first fluid outlet port 72. In this configuration, second fluid inlet port 73 is sealed and oxygen enriched, permeate air on the shell side is discharged through second fluid outlet port 74. The second fluid outlet port is preferably placed near the inlet plenum end of the membrane module.

Additional details of membrane structure suitable for use in this invention and methods of making membrane modules having a thin layer gas permeable membrane are disclosed in U.S. patent applications Ser No. 08/862,944 filed May 30, 1997, now U.S. Pat. No. 5,914,154, and 08/735,922 filed Oct. 24, 1996, now U.S. Pat. No. 5,876,604, the complete disclosures of which are incorporated herein by reference.

It can readily be appreciated that many variations in the modes of operation, number, shape and placement of membrane module elements are suitable for use in the present invention. Variations to the embodiment shown in FIG. 6 which are contemplated as falling within the breadth of the present invention include, for example, (a) coating the amorphous copolymer coating on the exterior surface of the hollow fiber or on both interior and exterior surfaces; and (b) conducting the incoming ambient air through the shell side and causing the oxygen enriched air to permeate into the tube side.

The blower used in this invention can be any of various types of fans well known in the art such as a straight, forward curved or backward curved centrifugal fan, axial flow fan, rotary vane pump, piston compressor, diaphragm compressor, linear pump and rocking arm pump. A centrifugal fan is preferred for high energy efficiency. Preferably, the blower size is selected to provide at least two times the desired permeate stream flow, and more preferably at least five times the permeate flow.

It is preferred to utilize a rocking arm piston vacuum pump due to high energy efficiency. Any other type of vacuum pump can be used, such as a rotary vane pump, piston vacuum pump, liquid seal vacuum pump and linear vacuum pump.

In connection with selecting the blower and vacuum pump weight is also an important consideration in view of a goal to maintain the overall weight of the oxygen enriched air supply apparatus as low as possible for maximum portability. Recognizing that the air passing through these air moving units will be used for breathing, it is a further concern that the blower and vacuum pump do not contaminate the air. Accordingly, it is desirable to select a blower and pump which do not use liquid seal lubricants, especially oil or toxic liquid based lubricants. If a liquid lubricated pump is used, attention should be paid to assuring that the lubricant is non-toxic and that the lubricant does not normally enter the air stream.

Any type of gas accumulator well known in the art of gas transfer tube pressure surge damping can be used for the gas reservoir. As is understood in the art, the volume of a pulsation damping accumulator is large compared to the volume of the gas transfer tube. Preferably, the volume of the gas reservoir should be at least about four times the combined volume of the reservoir outlet tube 11 and breathing tube 13, and more preferably at least about ten times the combined volumes.

Representative gas reservoir devices include a simple, single compartment, rigid wall, fixed volume, gas containment vessel, a vessel with pressure or spring loaded diaphragm, a spring activated, bellows, and an elastically deformable bladder. In the latter three example reservoir types, the reservoir has a variable volume defined by the diaphragm, bellows or bladder wall. The diaphragm, bellows or bladder walls expand under action of spring, pressure or elastic loading to dampen the flow surges. The elastically deformable bladder is preferred.

With reference to FIG. 1A, a particular embodiment of a portable oxygen enriched air supply apparatus according to the present invention includes a Rotron Revaflow (Ametek Rotron Technical Motor Division, Rotron, Inc., Saugerties, N.Y.) 2 blower to supply ambient air drawn in through a 1.9 cm outside diameter thermoplastic urethane, wire reinforced, supply tube 1 to the tube side 22 of a hollow fiber membrane module (Compact Membrane Systems, Wilmington, Del.) 4 via feed tube 3. The module was a model CMS-3 which had about 717 microporous polysulfone hollow fibers of 800 $\mu$m inner diameter and 22.2 cm effective length. The nonporous gas permeable membrane layer coating the inside of the hollow fibers was 65% PDD/35% tetrafluoroethylene ("TFE") copolymer. Average thickness of the PDD/TFE coating was about 0.2 $\mu$m. The module thus had about 4,000 cm$^2$ of total membrane surface area 26 which was rated to provide an oxygen flux rate of 1470 GPU at an oxygen/nitrogen selectivity of 2.52.

A Model 8006-0427-BLDC Boxer 24 VDC vacuum pump 6 (Thomas Industries, Inc., Sheboygan, Wis.) withdrew from the module shell side 24 oxygen enriched air. Nitrogen enriched air was discharged from the tube side via vent 5. Vacuum pump exit permeate was fed to a fluted, 1 liter, double ended Neoprene® rubber bladder 8 (Ferraris Medical Inc., Toledo, Ohio). The bladder outlet tube 11 was equipped with a pressure relief valve 10 set to relieve to atmosphere through tube 9 if outlet tube pressure exceeded 8600 Pa. Bladder outlet tube 11 was connected to the inlet of conserver valve 12 which exhausted through tube 13 to a breathing nozzle for user 16. A pressure sensor 14 can detect a pressure perturbation in tube 13 at start of inhalation and can transmit a signal via connection 15 to the conserver valve controller. Two 12 volt direct current Duracell DR36 batteries in series 30 were provided to power the vacuum pump utilizing conductors 31. A single DR36 battery 32 powered the blower and conserver valve operator utilizing conductor line 33. The apparatus also included on/off electric switch and other conventional electric circuitry (not shown). The ambient air intake of tube 1 can optionally be equipped with a filter to prevent obstruction of the apparatus by dust and other airborne particulates.

The nozzle at the discharge end of breathing tube 13 for feeding oxygen enriched air to the user can be any of the types well known in the art for this purpose. Representative examples include a breathing air mask, a breathing air isolation tent, and a two port cannula which basically has two small tubes split from the main tube and adapted to insert into the user's nostrils.

In operation, the blower 2 continuously blew 39 L/min. ambient air at 3,300 Pa (11.5 inches water) in tube 3. Vacuum pump 6 drew a vacuum of 67.5 KPa on the shell side 24 of module 4 which produced an 8 L/min. permeate flow of 30 vol. % oxygen enriched air which was fed to bladder 8. Normally, the conserver valve 12 was shut which blocked outlet flow from the bladder to the breathing nozzle. When a user 16 began to inhale through a nozzle inserted into the nostrils, a vacuum pulse was detected by sensor 14 which triggered the valve controller through connection 15 to open conserver valve 12 for 1.25 seconds. During the conserver valve open period, oxygen enriched air from the bladder flowed through tubes 11 and 13 to the user's nostrils. It was calculated that these conditions provided the equivalent of 1.8 L/min. pure oxygen. The apparatus was operated continuously for 1.25 hours which demonstrated that a supply of breathable oxygen enriched air could be provided to an individual with independence from a primary source of oxygen.

The weight of various components shown in FIG. 1A are stated in Table I. These components with tubing, circuitry, light weight frame and carry straps for a back pack configuration would have a total weight low enough that a typical person needing a supplemental supply of oxygen enriched air would be able to carry the portable apparatus.

TABLE I

|  | Weight (g) |
| --- | --- |
| Blower | 268 |
| Membrane Module | 119 |
| Vacuum Pump | 1284 |
| Bladder | 79 |
| Conserver valve | 332 |
| DR 36 batteries (total of 3) | 3279 |
| Total weight | 5361 |

Figure 2:
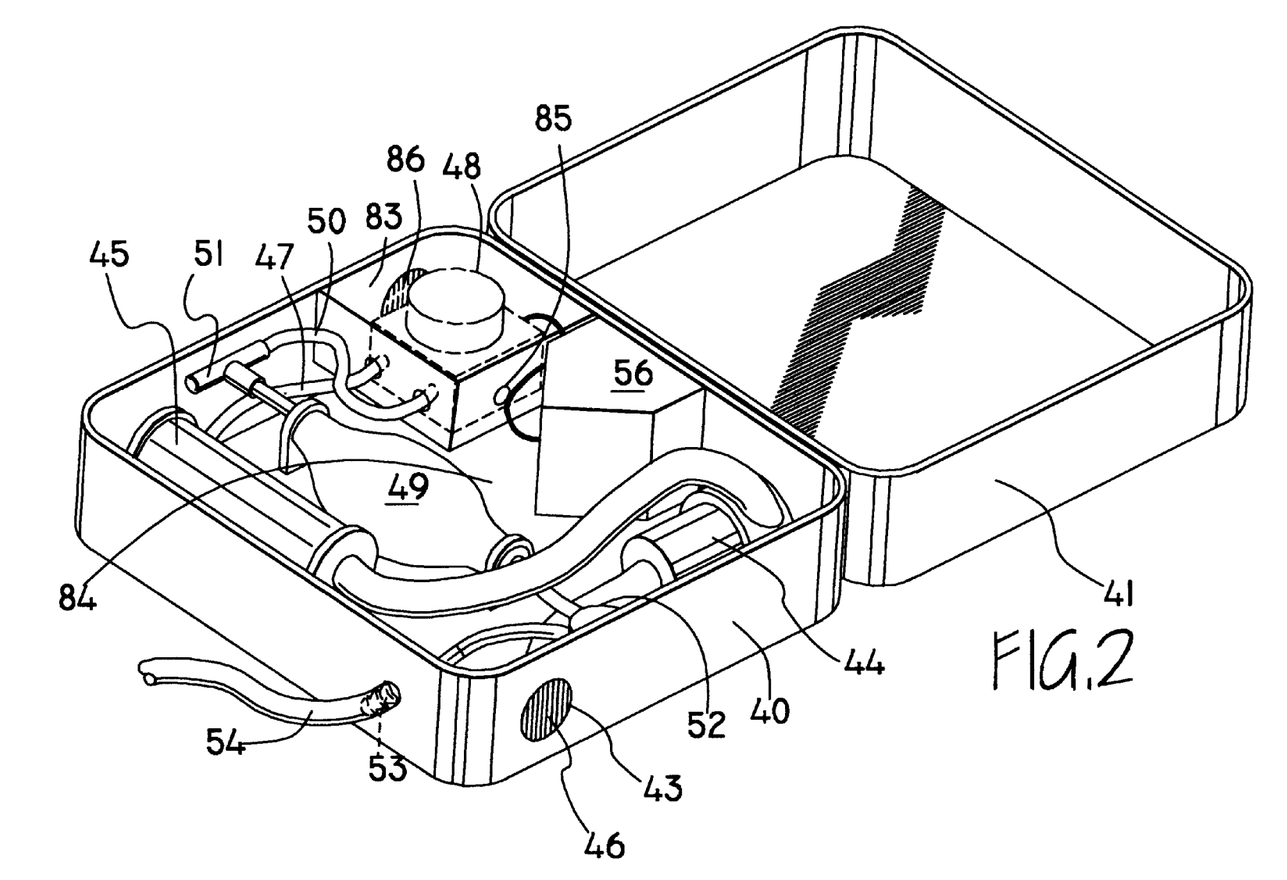
FIG. 2 is a perspective view of an embodiment of the novel portable oxygen enriched air supply apparatus showing the configuration of components within a case designed to be hand carried.
Figure 3:
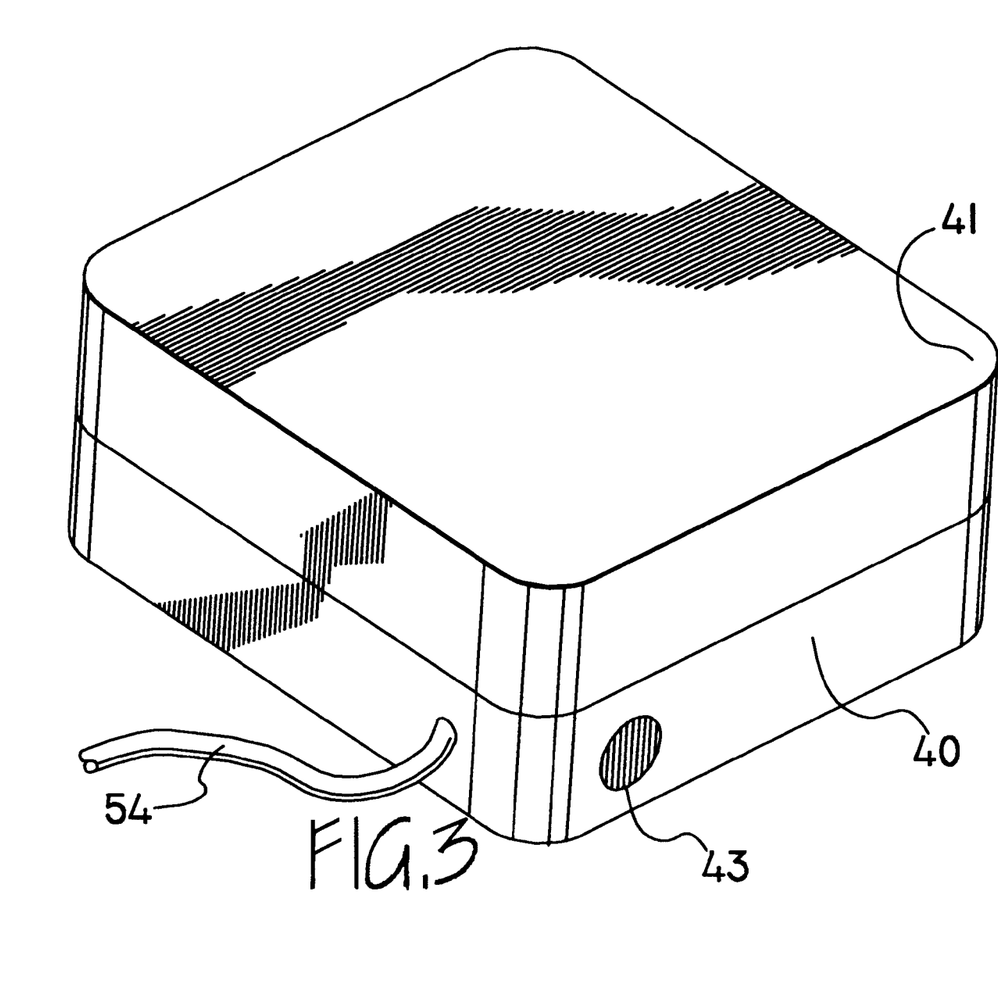
FIG. 3 is a perspective view of the apparatus of FIG. 2 showing the case closed.
Figure 4:
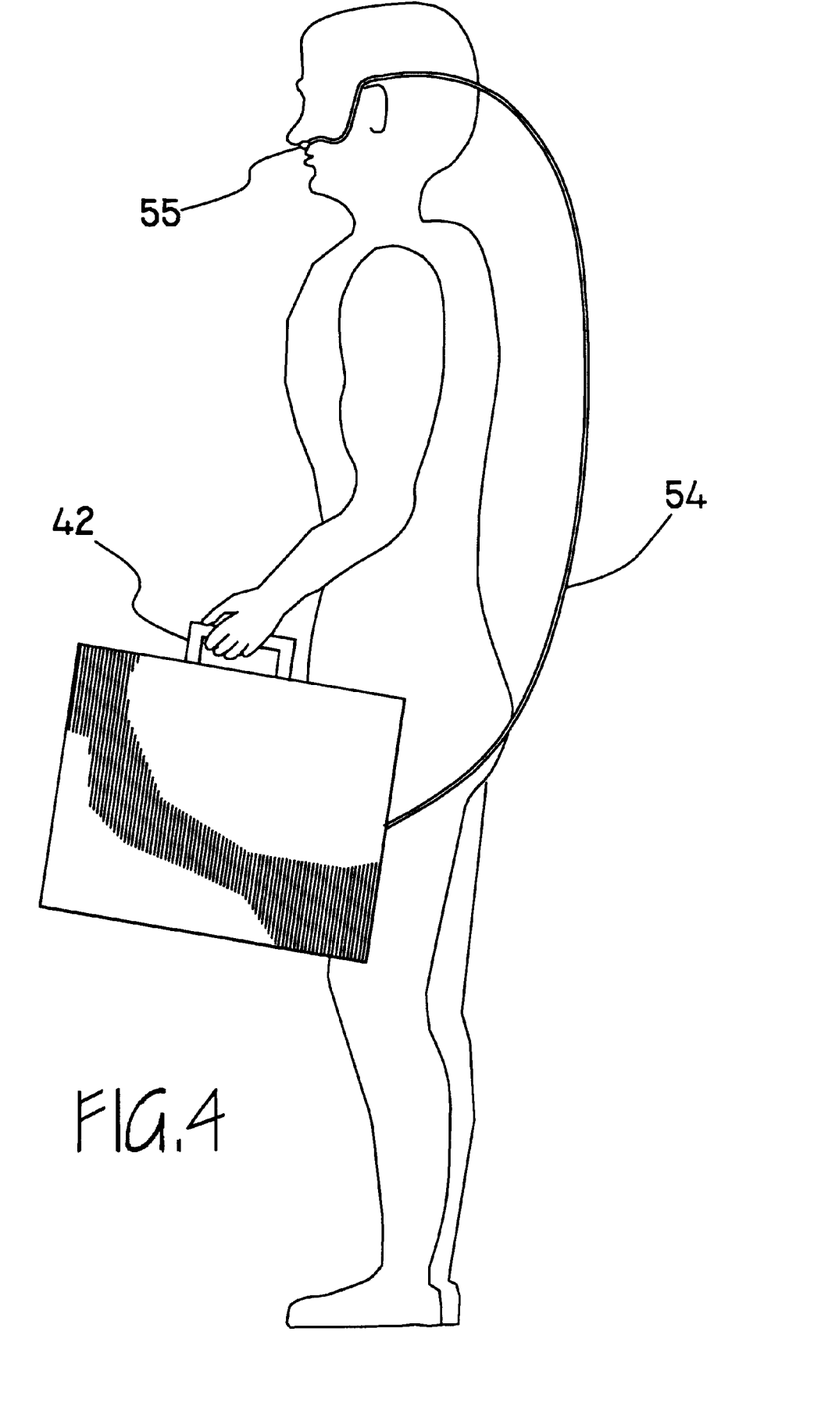
FIG. 4 is a perspective view showing the apparatus of FIGS. 2 and 3 in use.

The elements of the portable enriched air supply apparatus can be assembled in a self-contained unit for convenient transport by the user or the user's assistant during operation. In one aspect, the elements can be installed within a rigid, air tight case 40 as seen in FIGS. 2–4. The case includes a hinged or removable cover 41 for access to the apparatus elements for maintenance purposes. One or more handles 42 (FIG. 4) can be provided to allow the user to carry the apparatus by hand. Optionally, the case can be strapped to a separate pull cart or luggage wheels can be integrated into the case to facilitate transport.

With reference to FIGS. 2 and 3 it is seen that ambient air enters intake nozzle 43 in the wall of the case and is blown by blower 44 into the tube side of membrane module 45. The intake nozzle is covered with screen 46 to filter dirt, dust and similar contamination. Oxygen enriched permeate air is drawn from shell side nozzle (not seen) via tube 47 into the vacuum pump 48. The permeate is discharged from the pump into bladder 49 by way of tube 50 which contains a pressure relief valve 51. A conserver valve 52 is in the tube from the bladder exit leading to the breathing tube connection port 53 mounted on the case shell. The user can plug the breathing tube 54 into the connection port 53 then deploy the breathing air nozzle 55 (FIG. 4) to enable consumption of oxygen enriched air while carrying the unit in one hand. Electrical circuitry, including batteries 56, can be placed in the case. On/off switch and optional indicator lamp can be mounted on the shell of the case for convenient operation by the user. The case can also optionally include a sound dampening liner, for example of foam padding material.

Figure 5:
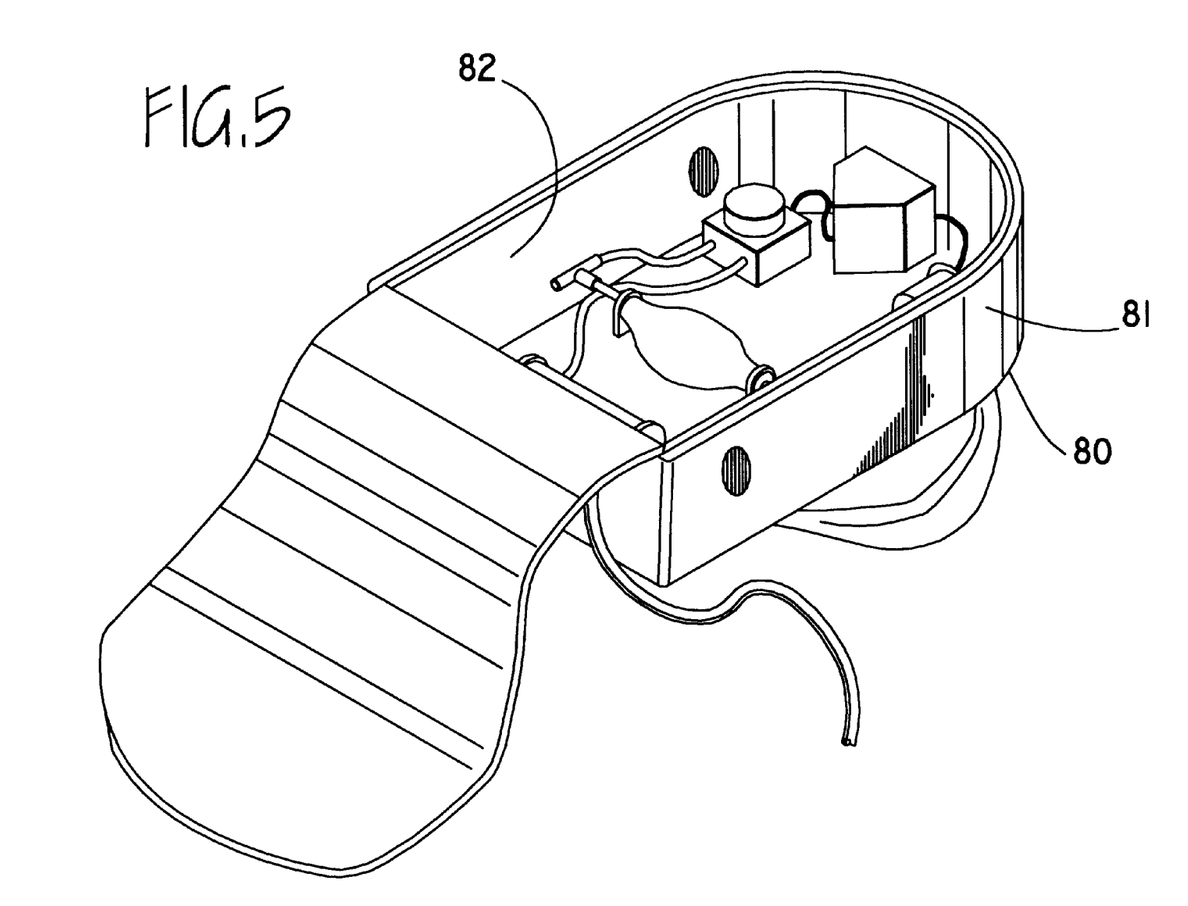
FIG. 5 is a perspective view of another embodiment of the novel portable oxygen enriched air supply apparatus showing the configuration of components within a case designed to be carried on one's back.
Figure 7:
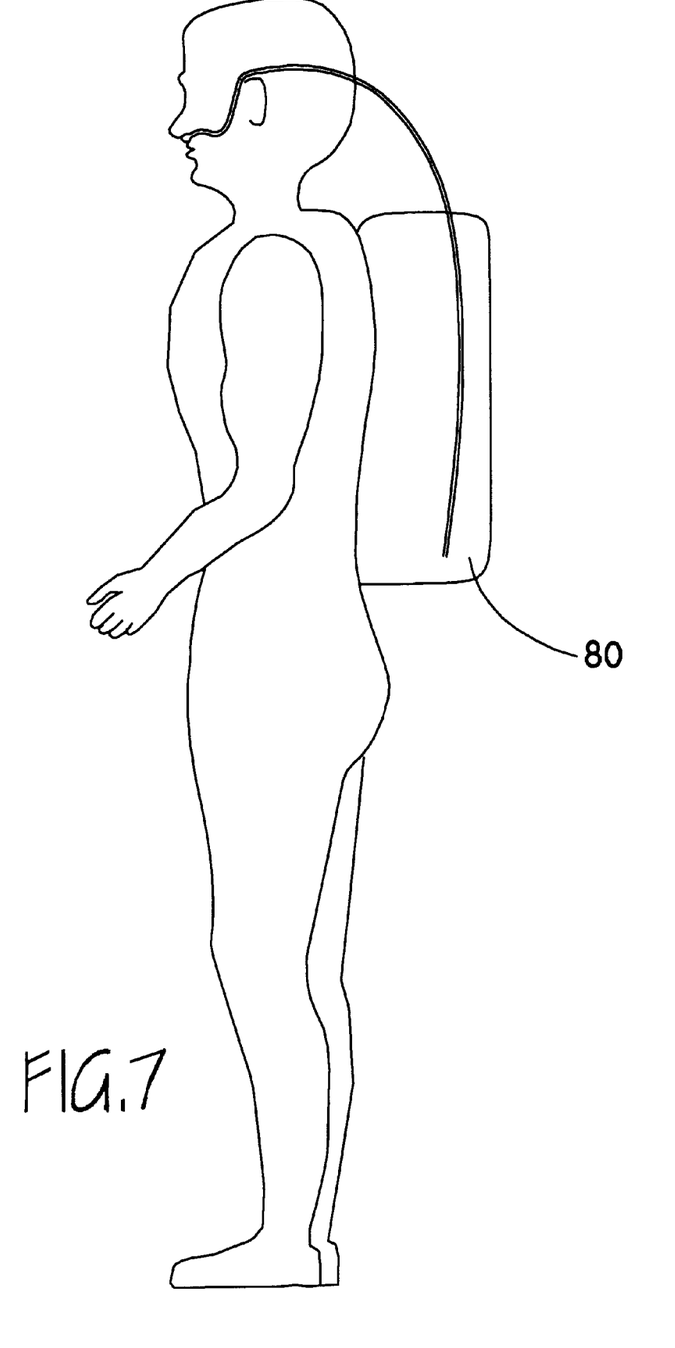
FIG. 7 is a perspective view of the apparatus of FIG. 5 in use.

In another aspect, the novel oxygen enriched air breathing apparatus can be assembled into a back pack case 80 adapted to be worn on the users back, as shown in FIGS. 5 and 7. For comfort, the shell 81 of the back pack case can be of fabric construction. The fabric case can be lined with a substantially air impermeable barrier layer film 82. This barrier layer forces the retentate cooling air discharged within the closed back pack to discharge through a vent port via the air-cooled compartment in the same manner as described below in connection with the rigid, hand held case.

With reference to FIG. 2 it is seen that preferably, the vacuum pump is installed in the case enclosed within an air-cooled compartment defined by a baffle 83. The inlet and outlet tubes to the vacuum pump and electrical wiring pass through the baffle which is otherwise sealed off from the main compartment 84 of the case except for baffle port 85. The air-cooled compartment also includes a vent port 86 in the exterior wall of the case. It can now be appreciated that nitrogen enriched retentate air discharges from the tube side of the membrane module through first fluid outlet port (not seen) to the main compartment then passes through baffle port 85 and into the air-cooled compartment. After passing over the vacuum pump and absorbing heat developed by the pump during operation, the air discharges to atmosphere through the vent port. To maximize cooling air contact with the pump, the baffle can be designed to conform closely to the shape of the vacuum pump with a generally narrow gap for cooling air flow between the pump and the baffle. A high cooling efficiency is thereby achieved. To bolster the structural strength of the assembly, the pump can be affixed to the baffle, provided that attachment means do not substantially interfere with the flow of cooling air around the pump. Placing the vacuum pump inside the air-cooled compartment advantageously provides cooling of the vacuum pump without the need of furnishing a second cooling fan and associated power source therefor. By eliminating these additional elements, the overall size of the unit can be kept small, and very importantly, the weight can be maintained extremely low.

While primarily directed to treatment of chronic breathing problems, the present invention also can be used to treat short term medical conditions. For example, the portable apparatus may be useful to assist recovery from shortness of breath upon brief but excessively vigorous physical exertion. The novel oxygen enriched air supply apparatus can be used to provide enriched breathing air to humans or other animals.

Although specific forms of the invention have been selected for illustration in the drawings and the preceding description is drawn in specific terms for the purpose of describing these forms of the invention, this description is not intended to limit the scope of the invention which is defined in the claims.

What is claimed is:

1. A process comprising the steps of
   (a) feeding ambient air to an apparatus comprising
       a membrane separation module comprising an oxygen gas selectively permeable membrane defining within the module a retentate chamber on one side of the membrane and a permeate chamber on the opposite side of the membrane;
       an ambient air intake fan having an exhaust port in fluid communication with the retentate chamber;
       a vacuum pump having a suction port and a discharge port, the suction port being in fluid communication with the permeate chamber;
       breathing nozzle means for delivering oxygen enriched air to an animal; and
       a gas transfer tube extending to the breathing nozzle means
   in which the membrane separation module, ambient air intake fan, and vacuum pump are positioned in a case comprising (i) an internal baffle defining an air-cooled chamber in which the vacuum pump is located and a main chamber in which the module is located, which internal baffle conforms closely in shape to the vacuum pump with a narrow air gap between the pump and baffle and which internal baffle has a baffle port in fluid connection between the air-cooled chamber and the main chamber but otherwise separates the two chambers, and (ii) an air vent port from the air-cooled chamber through the case to outside atmosphere, and
   in which the retentate chamber of the membrane separation module comprises an outlet port in fluid communication with the main chamber of the case, the outlet port being adapted to discharge retentate air from the membrane separation module into the main chamber, through the baffle port into the air-cooled chamber within the narrow air gap and out to the outside atmosphere through the air vent port
   (b) producing oxygen enriched air in the apparatus, and
   (c) supplying the oxygen enriched air to breathing air of an animal.

2. A process comprising the steps of
   (a) feeding ambient air to an apparatus comprising
       a membrane separation module comprising an oxygen gas selectively permeable membrane defining within the module a retentate chamber on one side of the membrane and a permeate chamber on the opposite side of the membrane;
       an ambient air intake fan having an exhaust port in fluid communication with the retentate chamber;
       a vacuum pump having a suction port and a discharge port, the suction port being in fluid communication with the permeate chamber;
       gas reservoir means for storing oxygen enriched air received from the discharge port;
       breathing nozzle means for delivering oxygen enriched air to an animal;
       a gas transfer tube extending from the reservoir means to the breathing nozzle means
       a conserver valve in the gas transfer tube intermediate the reservoir means and the breathing nozzle means;
       sensor means in the gas transfer tube downstream of the conserver valve for detecting the start of inhalation by the consumer; and
       control means for operating the conserver valve to be open only for a portion of the breathing cycle which starts at commencement of inhalation by the animal;
   (b) producing oxygen enriched air in the apparatus, and
   (c) supplying the oxygen enriched air to breathing air of an animal.

3. The process of claim 2 in which the apparatus further comprises a case defining a main chamber which comprises an air-cooled chamber in which the vacuum pump is located, the internal air-cooled chamber being defined by an internal baffle separating the air-cooled chamber from the main chamber, the baffle closely conforming in shape to the vacuum pump with a narrow air gap between the pump and baffle, in which the air-cooled chamber comprising an air vent port through the carrying case to outside atmosphere, and in which the retentate chamber of the membrane separation module comprises an outlet port in fluid communication with the main chamber of the case, which process further comprises the steps of causing air from the outlet port to flow into the main chamber, passing said air through the baffle port into the air-cooled chamber, thereby cooling the vacuum pump, and exhausting said air to atmosphere through the air vent port.

4. The process of claim 2 in which the apparatus further comprises at least one battery and the process comprises the step of transporting the apparatus by a person while the apparatus supplies breathing air to a person.

5. The process of claim 2 in which the gas transfer tube has a tube volume and the gas reservoir has a reservoir volume at least multiple times the tube volume.

6. The process of claim 5 in which the reservoir volume is at least four times the tube volume.

7. The process of claim 2 which comprises the step of opening the conserver valve only for a preselected duration after start of inhalation by the animal.

8. A process comprising the steps of
   (a) feeding ambient air to an apparatus comprising
       a membrane separation module comprising an oxygen gas selectively permeable membrane defining within the module a retentate chamber on one side of the membrane and a permeate chamber on the opposite side of the membrane;
       an ambient air intake fan having an exhaust port in fluid communication with the retentate chamber;
       a vacuum pump having a suction port and a discharge port, the suction port being in fluid communication with the permeate chamber;
       breathing nozzle means for delivering oxygen enriched air to an animal;
       a gas transfer tube extending from the discharge port to the breathing nozzle means;
       a conserver valve in the gas transfer tube;
       sensor means in the gas transfer tube downstream of the conserver valve for detecting the start of inhalation by the animal; and
       control means for operating the conserver valve to be open only for a portion of the breathing cycle which starts at commencement of inhalation by the animal
   (b) producing oxygen enriched air in the apparatus, and
   (c) supplying oxygen enriched air to breathing air of an animal.

9. The process of claim 8 which comprises the step of opening the conserver valve only for a preselected duration after start of inhalation by the animal.

10. An oxygen enriched air supply apparatus comprising a membrane separation module comprising an oxygen gas selectively permeable membrane defining within the module a retentate chamber on one side of the membrane and a permeate chamber on the opposite side of the membrane;

an ambient air intake fan having an exhaust port in fluid communication with the retentate chamber;

a vacuum pump having a suction port and a discharge port, the suction port being in fluid communication with the permeate chamber;

breathing nozzle means for delivering oxygen enriched air to an animal; and a gas transfer tube extending to the breathing nozzle means;

in which the membrane separation module, ambient air intake fan, and vacuum pump are positioned in a case comprising (i) an internal baffle defining an air-cooled chamber in which the vacuum pump is located and a main chamber in which the module is located, which internal baffle conforms closely in shape to the vacuum pump with a narrow air gap between the pump and baffle and which internal baffle has a baffle port in fluid connection between the air-cooled chamber and the main chamber but otherwise separates the two chambers, and (ii) an air vent port from the air-cooled chamber through the case to outside atmosphere, and in which the retentate chamber of the membrane separation module comprises an outlet port in fluid communication with the main chamber of the case, the outlet port being adapted to discharge retentate air from the membrane separation module into the main chamber, through the baffle port into the air-cooled chamber within the narrow air gap and out to the outside atmosphere through the air vent port.

11. An oxygen enriched air supply apparatus comprising a membrane separation module comprising an oxygen gas selectively permeable membrane defining within the module a retentate chamber on one side of the membrane and a permeate chamber on the opposite side of the membrane;

an ambient air intake fan having an exhaust port in fluid communication with the retentate chamber;

a vacuum pump having a suction port and a discharge port, the suction port being in fluid communication with the permeate chamber;

gas reservoir means for storing oxygen enriched air received from the discharge port;

breathing nozzle means for delivering oxygen enriched air to an animal;

a gas transfer tube extending from the reservoir means to the breathing nozzle means;

a conserver valve in the gas transfer tube intermediate the reservoir means and the breathing nozzle means;

sensor means in the gas transfer tube downstream of the conserver valve for detecting the start of inhalation by the animal; and control means for operating the conserver valve to be open only for a portion of the breathing cycle which starts at commencement of inhalation by the animal.

12. The apparatus of claim 11 in which the membrane separation module includes a plurality of open ended, microporous hollow fibers defining inner surfaces and outer surfaces, all of at least one of said surfaces being coated with a continuous layer formed from an amorphous copolymer of perfluoro-2,2-dimethyl-1,3-dioxole and having a permeability to oxygen of at least 100 barrers at a temperature below the glass transition temperature of the amorphous copolymer, the hollow fibers extending between two tube sheets in substantially parallel alignment within a casing.

13. The apparatus of claim 11 in which the gas reservoir means comprises at least one selected from an elastically deformable bladder, a diaphragm, a rigid wall fixed volume vessel, and a bellows.

14. The apparatus of claim 13 in which the gas reservoir means comprises a rigid wall fixed volume vessel.

15. The apparatus of claim 11 further comprising a power connection means for providing electrical power from an external source of standard alternating current electricity or from an external source of direct current electricity to operate the oxygen enriched air supply apparatus.

16. The apparatus of claim 11 further comprising at least one battery capable of providing electrical power to operate the apparatus in portable mode.

17. The apparatus of claim 16 in which the membrane separation module, ambient air intake fan, vacuum pump, gas reservoir means and battery are assembled in a case adapted for a person to carry the apparatus during operation.

18. The apparatus of claim 17 in which the case defines a main chamber and which case comprises an air-cooled chamber in which the vacuum pump is located, the air-cooled chamber being defined by an internal baffle having a baffle port in fluid communication between the air-cooled chamber and the main chamber but otherwise separating the air-cooled chamber from the main chamber, the baffle closely conforming in shape to the vacuum pump with a narrow air gap between the pump and baffle, and the air-cooled chamber comprises an air vent port through the carrying case to outside atmosphere.

19. The apparatus of claim 18 in which the retentate chamber of the membrane separation module comprises an outlet port in fluid communication with the main chamber of the carrying case, thereby enabling retentate air flow to discharge into the main chamber, pass through the baffle port into the air-cooled chamber and exhaust to the outside atmosphere through the air vent port.

20. The apparatus of claim 16 in which the battery is a rechargeable battery or a replaceable battery.

21. The apparatus of claim 20 which further comprises electric component means for permitting operating of the apparatus or recharging batteries from standard alternating current electricity or from a source of auxiliary direct current electricity.

22. The apparatus of claim 2 in which the gas transfer tube has a tube volume and the gas reservoir has a reservoir volume at least multiple times the tube volume.

23. The apparatus of claim 22 in which the reservoir volume is at least four times the tube volume.

24. The apparatus of claim 11 in which the control means is adapted for operating the conserver valve to be open only for a preselected duration after start of inhalation by the animal.

25. An oxygen enriched air supply apparatus comprising a membrane separation module comprising an oxygen gas selectively permeable membrane defining within the module a retentate chamber on one side of the membrane and a permeate chamber on the opposite side of the membrane;

an ambient air intake fan having an exhaust port in fluid communication with the retentate chamber;

a vacuum pump having a suction port and a discharge port, the suction port being in fluid communication with the permeate chamber;

breathing nozzle means for delivering oxygen enriched air to an animal;

a gas transfer tube extending from the discharge port to the breathing nozzle means;

a conserver valve in the gas transfer tube;

sensor means in the gas transfer tube downstream of the conserver valve for detecting the start of inhalation by the animal; and control means for operating the conserver valve to be open only for a portion of the breathing cycle which starts at commencement of inhalation by the animal.

26. The apparatus of claim 25 further comprising a pressure relief valve in the gas transfer tube upstream of the conserver valve.

27. The apparatus of claim 25 further comprising a power connection means for providing electrical power from an external source of standard alternating current electricity or from an external source of direct current electricity to operate the oxygen enriched air supply apparatus.

28. The apparatus of claim 25 further comprising at least one battery capable of providing electrical power to operate the apparatus in portable mode.

29. The apparatus of claim 28 in which the membrane separation module, ambient air intake fan, vacuum pump and battery are assembled in a case adapted for a person to carry the apparatus during operation.

30. The apparatus of claim 29 in which the case defines a main chamber and which case comprises an air-cooled chamber in which the vacuum pump is located, the internal air-cooled chamber being defined by an internal baffle having a baffle port in fluid communication between the air-cooled chamber and the main chamber but otherwise separating the air-cooled chamber from the main chamber, the baffle closely conforming in shape to the vacuum pump with a narrow air gap between the pump and baffle, in which the air-cooled chamber comprises an air vent port through the carrying case to outside atmosphere, and in which the retentate chamber of the membrane separation module comprises an outlet port in fluid communication with the main chamber of the carrying case, thereby enabling retentate air flow to discharge into the main chamber, pass through the baffle port into the air-cooled chamber and exhaust to atmosphere through the air vent port.

31. The apparatus of claim 25 in which the control means is adapted for operating the conserver valve to be open only for a preselected duration after start of inhalation by the animal.

* * * * *

UNITED STATES PATENT AND TRADEMARK OFFICE
CERTIFICATE OF CORRECTION

PATENT NO : 6,126,721
DATED : October 3, 2000
INVENTOR(S) : Nemser et al.

It is certified that error appears in the above-identified patent and that said Letters Patent are hereby corrected as shown below:

In claim 22, at line 1, delete "claim 2" and substitute -- claim 11 -- therefor.

Signed and Sealed this

Twenty-fourth Day of April, 2001

Attest:

NICHOLAS P. GODICI

Attesting Officer    Acting Director of the United States Patent and Trademark Office

UNITED STATES PATENT AND TRADEMARK OFFICE
CERTIFICATE OF CORRECTION

PATENT NO. : 6,126,721
DATED : October 3, 2000
INVENTOR(S) : Stuart Nemser et al.

It is certified that error appears in the above-identified patent and that said Letters Patent is hereby corrected as shown below:

Column 1,
Below the title, insert the following paragraph:
-- This invention was made with Government support under contract number R43 HL51765 awarded by the National Institute of Health. The Government has certain rights in the invention. --

Signed and Sealed this

Second Day of October, 2001

Attest:

*Nicholas P. Godici*

NICHOLAS P. GODICI
*Attesting Officer*    *Acting Director of the United States Patent and Trademark Office*